(12) United States Patent
Sundrehagen et al.

(10) Patent No.: US 7,279,283 B1
(45) Date of Patent: Oct. 9, 2007

(54) COBALAMIN ASSAY (75) Inventors: Erling Sundrehagen, Oslo (NO); Lars Orning, Oslo (NO)

(73) Assignee: Axis-Shield ASA, Oslo (NO)

( * ) Notice: Subject to any disclaimer, the term of this patent is extended or adjusted under 35 U.S.C. 154(b) by 0 days.

(21) Appl. No.: 09/679,043

(22) Filed: Oct. 4, 2000

Related U.S. Application Data (63) Continuation of application No. PCT/GB99/03127, filed on Sep. 20, 1999.

(30) Foreign Application Priority Data

Sep. 18, 1998 (GB) ................................ 9820473.8

(51) Int. Cl.
*G01N 33/53* (2006.01)
*G01N 33/566* (2006.01)

(52) U.S. Cl. ........................... 435/7.1; 435/4; 435/7.5; 435/7.9; 435/7.92; 436/501; 436/518

(58) Field of Classification Search .................... 435/4, 435/14, 21, 25, 7.9, 7.93, 7.1, 7.92, 975, 435/7.5; 436/501–505, 127, 546, 545, 128, 436/544, 804, 131, 815, 825, 174, 91, 92, 436/93, 96, 175, 103, 104, 106, 111, 178, 436/811, 518; 424/1, 12; 23/230.3
See application file for complete search history.

(56) References Cited

U.S. PATENT DOCUMENTS

| 4,332,785 A | * | 6/1982 | Allen et al. ..................... 424/1 |
| 4,465,775 A | * | 8/1984 | Houts .......................... 436/503 |
| 4,680,273 A | * | 7/1987 | Herbert ........................ 436/92 |
| 5,310,656 A | | 5/1994 | Pourfarzaneh et al. ..... 435/7.93 |
| 5,374,560 A | | 12/1994 | Allen et al. ................. 436/129 |
| 5,451,508 A | * | 9/1995 | Hoyle et al. ............... 435/7.93 |
| 5,506,109 A | | 4/1996 | Pourfarzaneh et al. ..... 435/7.92 |

OTHER PUBLICATIONS

Morelli et al., "Raioimmunoassay for serum transcobalamin II", The Journal of Laboratory and Clinical Medicine, Mar. 1977, vol. 89, No. 3, pp. 645-652.*
Maggio. Enzyme-Immunoassy. pp. 186-187, Copy write 1980 by CRC Press, Inc.*
Edward T. Maggio, Enzyme-Immunoassay, pp. 186-187, copywrite 1980 by CRC Press, Inc.*
Jacobsen et al. (Blood, vol. 55, No. 1, Jan. 1980, pp. 160-163).*
Frater-Schroeder et al. (Analytical Biochemistry, 1982, vol. 124, No. 1, pp. 92-101, Abstract Only).*
Steven C. Kuemmerle, et al., "Automated Assay of Vitamin B-12 by the Abbott IMx® Analyzer", Clin. Chem. 38/10, 2073-2077 (1992).
Gary R. McLean et al., "Antibodies to Transcobalamin II Block in Vitro Proliferation of Leukemic Cells", Blood, vol. 89, No. 1, Jan. 1, 1997, pp. 235-242.

Edward V. Quadros et al., "Characterization of Monoclonal Antibodies to Epitopes of Human Transcobalamin II", Biochemical and Biophysical Research Communications 222, 149-154, (1996), Article No. 0713.
S.N. Wickramasinghe, S. Fida, "Correlations between holo-transcobalamin II, holo-haptocorrin, and total B12 in serum samples from healthy subjects and patients", Department of Haematology, St. Mary's Hospital Medical School, J Clin Pathol 1993; 46:537-539.
Chemical Abstracts, Aug. 15, 1977, XP002127542 & E. Nexoe, "Characterization of the cobalamins attached to transcobalamin I and transcobalamin II in human plasma", Scandinavian Journal of Haematology, 1977.
Chemical Abstracts, Jun. 3, 1996, XP002127543 & E.V. Quadros et al., "Characterization of monoclonal antibodies to epitopes of human transcobalamin II", Biochemical and Biophysical Research Communications, 1996.
MEDLINE, Washington, D.C., XP002127541 & S.P. Rothenberg et al., "Transcobalamin II and the membrane receptor for the transcobalamin II-cobalamin complex", Baillieres Clinical Haematology, 1995.
Paul A. Seligman and Robert H. Allen, "Characterization of the Receptor for Transcobalamin II Isolated from Human Placenta", Sep. 6, 1977, Division of Hematology-Oncology, Department of Internal Medicine, Washington University School of Medicine, St. Louis, MO 63110 and the Division of Hematology, Department of Medicine, University of Colorado Medical Center, Denver CO 80262.
Victor Herbert et al., "Low Holotranscobalamin II is the Earliest Serum Marker for Subnormal Vitamin $B_{12}$ (Cobalamin) Absorption in Patients with AIDS", 1990, Wiley-Liss, Inc. pp. 132-139.
Ebba Nexo et al., "How to Diagnose Cobalamin Deficiency", Scand J. Clin Lab Invest 1994;54 (Suppl 219) pp. 61-75.
Haematology and Coagulation; XXIV Nordic Congress, Stockholm 1994, 44 "Haemoglobin $A_{1c}$ on the Hitachi 717 Analyser", A. Maki et al.; 45 "Measurement of TC-cobalamin, a marker of cobalamin deficiency", Bodil Toft et al.; 46 "Quality goals for blood glycated hemoglobin A1c", I.M. Penttila et al.; 47 "Serum transferring receptor is a new tool for diagnosis of iron deficiency anemia", Kari Punnonen et al., pp. 62-63.
Ebba Nexo et al., "Characterization of the Particulate and Soluble Acceptor for Transcobalamin II from Human Placenta and Rabbit Liver", Biochimica et Biophysica Acta, 628 (1980) 190-200.
Ebba Nexo, "Characterization of the Cobalamins Attached to Transcobalamin I and Transcobalamin II in Human Plasma", Scand J. Haematol (1977) 18, 358-360.

(Continued)

*Primary Examiner*—Long V. Le
*Assistant Examiner*—Lisa V. Cook
(74) *Attorney, Agent, or Firm*—Bacon & Thomas, PLLC (57) ABSTRACT

The invention provides an assay method for the determination of transcobalamin II (TC II) bound cobalamin in a body sample, comprising contacting a cell free sample of a body fluid with an immobilised or immobilizable specific binding ligand for TC II or cobalamin bound TC II (holo TC II), separating a ligand bound fraction from a non-ligand bound fraction and measuring the holo-TC II or TC-II bound cobalamin content therein.

14 Claims, 2 Drawing Sheets

OTHER PUBLICATIONS

Kuemmerle et al., "Automated Assay of Vitamin $B_{12}$ by the Abbott Imx® Analyzer", Clin. Chem. 38/10, 2073-2077 (1992).

S.N. Wickramasinghe, S. Fida, "Correlations between holo-transcobalamin II, holo-haptocorrin, and total $B_{12}$ in serum samples from healthy subjects and patients", J. Clin. Pathol 1993, 46 537-539.

Thu Vu et al., "New Assay for the Rapid Determination of Plasma Holotranscobalamin II Levels: Preliminary Evaluation in Cancer Patients", American Journal of Hematology 42:202-211 (1993).

Barry Herzlich and Victor Herbert, "Depletion of Serum Holotranscobalamin II An Early Sign of Negative Vitamin $B_{12}$ Balance", Laboratory Investigation, vol. 58, No. 3, pp. 332-337, 1988.

J. Lindemans et al., "Application of a simple immunoadsorption assay for the measurement of saturated and unsaturated transcobalamin II and R-binders", Clinica Chimica Acta, 132 (1983) 53-61.

J. van Kapel et al., "Application of heparin-conjugated Sepharose for the measurement of cobalamin-saturated and unsaturated transcobalamin II", Clinica Chimica Acra, 172 (1988) 297-310.

S. Benhayoun et al., "Method for the Direct Specific Measurement of Vitamin $B_{12}$ Bound to Tanscobalamin II in Plasma", Acta Haematol 1993:89:195-199.

Edward V. Quadros et al., "Characterization of Monoclonal Antibodies to Epitopes of Human Transcobalamin II", Biochemical and Biophysical Research Communiocations 22, 149-154 (1996), Article No. 0713.

Gary R. McLean et al., "Antibodies to Transcobalamin II Block in Vitro Proliferation of Leukemic Cells", The American Society of Hematology, 1997, pp. 235-242.

Sheldon P. Rothenberg, Edward V. Quadros, "Transcobalamin II and the membrane receptor for the transcobalamin II-cobalamin complex", B. Clinical Haematology, vol. 8, No. 3, Sep. 1995.

Soren K. Moestrup et al., "Megalin-mediated endocytosis of transcobalamin-vitamin-$B_{12}$ complexes suggests a role of the receptor in vitamin-$B_{12}$ homeostasis", Proc. Natl. Acad. Sci. USA, vol. 93, pp. 8612-8617, Aug. 1996, Medical Sciences.

* cited by examiner

COBALAMIN ASSAY

This application is a continuation of PCT/GB99/03127, filed Sep. 20, 1999, (of which the entire disclosure of the pending, prior application is hereby incorporated by reference).

BACKGROUND OF THE INVENTION

The present invention relates to assay methods for the determination of cobalamin or vitamin $B_{12}$ in a body fluid and in particular to assay methods for the metabolically active pool of cobalamin.

Cobalamin or vitamin $B_{12}$ is a water soluble vitamin which forms part of the vitamin B complex found in foods. The core molecule consists of a corrin ring of four pyrole units which surround the essential cobalt atom. Cobalamin is the only vitamin which cannot be synthesised by animals or plants and must be absorbed from food in the gut. It can however be stored in the liver. It is synthesised by micro-organisms, in particular by anaerobic bacteria and yeasts.

Cobalamin functions in vivo as a co-enzyme and cobalamin enzymes catalyse three types of reaction; (i) intra-molecular rearrangements, for example, the formation of succinyl CoA from L-methylmalonyl CoA, (ii) methylations, for example, the formation of methionine by methylation of homocysteine and (iii) reduction of ribonucleotides to deoxyribonucleotides in some micro-organisms. In mammals, only two enzymic reactions, those specifically mentioned in (i) and (ii) above are known to require cobalamin as a co-enzyme.

In the process of digestion, a salivary protein called haptocorrin, hereinafter referred to as HC (which is also referred to in the art as R-binder or transcobalamins I and III collectively) binds cobalamin in the upper gastrointestinal tract forming a complex which passes through the stomach. Pancreatic enzymes digest the cobalamin-haptocorrin (holo-HC) complex in the ileum, liberating cobalamin which is then bound to a protein called intrinsic factor, which is secreted by the gastric mucosa, to form a further complex. The cobalamin-intrinsic factor complex binds to a specific receptor in the lining of the terminal ileum, whereupon it is dissociated by a releasing factor and the cobalamin transported actively across the membrane of the ileum into the blood stream.

Cobalamin does not circulate in the body in a free form in an appreciable amount. Probably 99% or so of cobalamin is bound by one of the transcobalamin proteins (TC I-III) or albumin.

The protein believed to be responsible for transporting cobalamin to target tissues is transcobalamin II (TC II), a critical trace protein without which cobalamin cannot cross cell membranes. Despite this important metabolic function only about 6-25% of cobalamin in the serum is bound to TC II and most is carried by HC. TC II is a single chain polypeptide of 45 kDa found primarily in serum, seminal fluid and cerebro-spinal fluid. Cobalamin bound TC II or holo-TC II, attaches to specific receptors on cell membranes and once bound, the holo-TC II complex is taken into cells by pinocytosis.

TC II is synthesised by the liver, vascular endothelium, enterocytes, macrophages and fibroblasts and circulates predominantly as apo-TC II, i.e. lacking bound cobalamin. It has a short half life of approximately 90 minutes.

Less than a quarter of the total plasma cobalamin is associated with TC II. The rest is bound to the other transcobalamins or albumin as mentioned above.

Since cobalamin must be absorbed from food, any conditions which result in impaired gastric function, for example, gastroenteritis or conditions resulting in gastric atrophy, or an inability to produce functional haptocorrin, intrinsic factor, releasing factor, TC II or TC II receptors, can result in impaired uptake of cobalamin and resultant deficiency.

Certain population sub-groups, for example the aged, pregnant women, patients with chronic or acute gastrointestinal disease, those suffering from certain autoimmune diseases, those with a family history of pernicious anaemia and AIDS sufferers, are particularly prone to cobalamin deficiency.

The clinical manifestations of cobalamin deficiency are varied and numerous but primarily involve, anaemia, megaloblastic haematopoiesis and functional and structural disorders of the nervous system. Around 60% of individuals diagnosed as being deficient in cobalamin are anaemic, but in many, neurological symptoms are the only clinical signs observed. Around 10% of patients exhibit psychiatric symptoms and around 40% exhibit both neurological and psychiatric symptoms.

Early diagnosis of cobalamin deficiency is crucial to ensure a good prognosis for patients, since some of the manifestations of cobalamin deficiency, particularly the neuropsychiatric effects, are irreversible if not detected and alleviated by cobalamin therapy quickly.

It is desirable therefore to accurately assess the cobalamin level of an individual in an expedient and efficient manner, with a view to establishing whether or not the individual may be suffering from cobalamin deficiency.

Measurement of total plasma cobalamin ie. cobalamin (and cobalamin like substances) bound to any one of the transcobalamin (TC) proteins I, II and III, has been used in attempts to assess cobalamin deficiency. This technique results in a broad based concentration distribution within a population which is considered to be normal and hence produces a wide reference range. Within individuals however, the range of available cobalamin considered to be normal for that individual, is very narrow. It has been observed that although an individuals metabolically active cobalamin concentration has moved outside their own reference range, their total plasma cobalamin content remains within the range considered to be normal for the population. Under such circumstances, cobalamin deficiency can go undetected. Such an unreliable method is clearly undesirable and it is well recognised that such serum or plasma cobalamin measurements have low diagnostic sensitivity and specificity.

Microbial assays involving micro-organisms dependent upon cobalamin for growth, have been developed and used in measuring plasma cobalamin concentration, but in addition to the difficulty of estimating the appropriate reference range, these methods require extraction and conversion of the cobalamins which is very time consuming, troublesome and wholly unsuited for rapid laboratory screening.

Alternative methods for assessing cobalamin deficiency involve measuring the accumulation of metabolites in the plasma which require cobalamin for their conversion. Plasma methylmalonate and plasma homocysteine levels increase in cobalamin deficient individuals (Chanarin, The megaloblastic anaemia; London, Blackwell Scientific Publications, 1991) and make good candidate molecules for correlation with vitamin $B_{12}$ deficiency. Methods based on homocysteine assessment have been shown, however, to be complicated, impractical and show poor specificity and sensitivity. Whilst methods based on methylmalonate measurement are accurate and reliable, they are cumbersome and require analysis by combined gas-chromatography/mass-spectrometry and are hence expensive and again unsuitable for routine clinical screening (Nexø et al. (1994) Scand. J. Clin. Lab. Invest. 54:61-76).

It has also been suggested that measurement of TC II bound cobalamin as opposed to total plasma cobalamin may provide a reliable clinical indictor of the likelihood of cobalamin deficiency (Herbert et al. (1990) Am. J. Hematol. 34:132-139; Wickramasinghe and Fida (1993) J. Clin. Pathol. 46:537-539; U.S. Pat. No. 4,680,273). However, such efforts to determine holo-TC II concentratration have to date been mostly indirect, estimating holo-TC II concentration as the difference between total plasma cobalamin and the cobalamin concentration of TC II depleted plasma.

Such TC II depletion may be accomplished by adsorption to ammonium sulphate (Carmel (1974) Am. J. Clin. Pathol. 62:367-372), microsilica (Herzlich & Hubert (1988) Lab. Invest. 58:332-337; Wickramasinghe & Fida (1993) J. Clin. Pathol. 46:537-539), microfine glass (Vu et al. (1993) Am. J. Hematol. 42:202-211) or immobilized anti-TC II polyclonal antibodies (Lindemans et al. (1983) Clin. Chim. Acta 132:53-61). The concentration of cobalamin in total plasma and the depleted fraction is performed by methods well known in the art such as radio or enzyme immunoassay techniques. These methods are unsuitable for routine screening automated or not automated because they are complex and time consuming and because the low degree of specificity of the adsorptive materials used results in insufficient separation of holo-TC II and holo-HC resulting in an overestimation of holo-TC II. Lot-to-lot variation of the adsorptive material introduces further errors and most importantly, the subtraction of one large volume from another large volume results in unacceptable inaccuracies and unreliability.

The other attempts to assess TC II have involved separating TC II from other serum components, including the TC I and TC III, using its lipophilicity. Thus Kapel et al. (1988) Clin. Chim. Acta 172:297-310, Benhayoun et al. (1993) Acta Haematol. 89:195-199 and Toft et al. (1994) Scand. J. Clin. Lab. Invest. 54:62 disclose methods for separating TC II from other transcobalamins using heparin sepharose, silica gel or cellulose respectively. These methods however suffer from the same disadvantages as the indirect methods since they rely on the same adsorptive materials. Also, the low plasma concentration of holo-TC II renders these methods unsuitable for combination with existing methods of cobalamin quantification. The normal range of holo-TC II is 35-160 pM and values below 35 pM would generally be considered as indicative of cobalamin deficiency. The reported analytical sensitivity of most routine methods for plasma cobalamin is about 40 pM but in practice it is often much higher, typically around 90 pM. Hence, normal plasma levels of holo-TC II are below or near the sensitivity limit of the routine methods for cobalamin quantification.

Possibly the most accurate method currently recognised for determining TC II bound cobalamin involves adsorbing TC II to silica and then assaying the bound fraction for cobalamin content using either an immunoassay as described for example by Kuemmerle et al. (1992) Clin. Chem. 38/10: 2073-2077, or a microbiological assay, the latter apparently producing the best results. This method requires an entire working day to perform only twenty assays. It is very expensive and impractical and poorly suited to routine clinical diagnostic laboratory investigations.

Thus, there exists a great need for improved methods of assessing the level of metabolically active cobalamin in a body fluid, with a view to correlating the cobalamin level with the likelihood of cobalamin deficiency, which are amenable to routine clinical diagnostic application.

SUMMARY OF THE INVENTION

Thus, according to a first aspect, the present invention provides an assay method for the determination of transcobalamin II bound cobalamin in a body sample, comprising contacting a cell free sample of a body fluid with an immobilised or immobilizable specific binding ligand for TC II or holo TC II, separating a ligand bound fraction from a non-ligand bound fraction and measuring the holo-TC II or TC-II bound cobalamin content therein.

DETAILED DESCRIPTION OF THE INVENTION

By a specific binding ligand is meant one which binds to TC II (ie. apo-TC II and holo-TC II) or holo TC II by virtue of its specific chemical structure or conformation and not simply by virtue of an overall physico-chemical property (such as lipophilicity) which may be common to many components of a body fluid sample. The binding affinity and specificity of the ligands suitable for use in the method preferably allow for a 3-fold, more preferably a 5-fold and even more preferably a 10-fold and most preferably a greater than 10-fold concentration of the TC II or holo-TC II in the sample and hence such a method is able to give accurate and reliable values for holo-TC II in the lower normal range of holo-TC II and also in the sub-normal range. Such a separation and concentration of the target molecules is not possible with currently existing methods which are unable to efficiently separate TC II or holo-TC II from HC or holo-HC. The ability to concentrate the TC II or holo-TC II at least 3-fold allows the use of automated analytical equipment in the performance assay. Without such a concentrating step, the amount of analyte present in a sample is likely to be below the lower detection limit. Such automated analytical equipment typically requires between 40 and 100 µl of sample in a total volume of typically 150 µl or greater for its operation. Thus, a low concentration analyte is diluted even further for analysis. By using the assay method of the invention however, the analyte is concentrated at least 3-fold. Since using such automated analytical equipment typically involves a control range of 100-700 pM with a lower sensitivity limit of about 40 pM but a practical lower limit of around 90 pM, a 5-fold concentration facilitates the measurement of holo-TC II at down to 18 pM and 10-fold concentration facilitates measurement down to 9 pM holo-TC II. Since the present invention facilitates concentration of greater than 10-fold it will be easily understood by the skilled person the extent to which sensitivity is enhanced making it a very powerful technique indeed.

The ability to concentrate the analyte so that it is amenable to analysis by such automated procedures is an important advantage of the present assay method.

Preferably from a 600 µl starting sample of body fluid, a volume of up to 150 µl, more preferably up to 100 µl and most preferably less than 60 µl will be generated which may then be analysed, optionally using automated procedures.

Any TC II specific binding ligand may be used in the method of the invention as either a capturing, concentrating and separating ligand or a detecting ligand, and depending on the specific embodiment of the invention may bind to TC II in both the apo and holo form or it may bind specifically or preferentially to the holo-form. The TC II binding ligand will preferably exhibit a high degree of selectivity and specificity towards TC II and will exhibit low or more preferably, essentially no affinity towards other TC proteins, ie. TC I or III, in either apo or holo form, or any other cobalamin-binding protein. If the TC II binding ligand is a holo-TC II specific binding ligand, the same properties are exhibited with the additional requirement that low or preferably no affinity is shown towards apo-TC II.

The TC II or holo-TC II binding ligand will generally be either an antibody, an antibody fragment or a compound with an affinity for TC II or holo-TC II respectively such as a cell surface receptor, a polypeptide, an oligopeptide, a small organic chemical, etc. Other binding ligands may be a specific binder selected from a combinatorial chemistry or phage display library or a specifically binding sequence of DNA or RNA.

If the binding ligand is an antibody it may be polyclonal but will preferably be monoclonal. Monoclonal antibodies can be generated with much greater specificity and uniformity than polyclonal antibodies and this reduces cross-reactivity with other components of the body fluid, in particular other transcobalamins and where appropriate, the alternative conformation ie. the apo form of the target analyte. The uniformity and reproducibility offered by monoclonal antibodies relative to polyclonal antibodies ensures a greater accuracy which is vital for an assay wherein the analyte is in such low concentration. Alternatively, it may be an antibody fragment for example F(ab), F(ab')$_2$ or F(v) fragment. The antibodies or antibody fragments may be monovalent or divalent and may be produced by hybridoma technology or be of synthetic origin, and generated by recombinant DNA technology or chemical synthesis. Single chain antibodies or other antibody derivatives or mimics could for example be used. The antibody may be directed or raised against any epitope, component or structure of the TC II or holo-TC II protein as appropriate.

Suitable antibodies for use as binding ligands in the present invention are disclosed for example by Quadros et al. (1996) Biochem. Biophys. Res. Commun. 222:149-154; M$^c$Lean et al. (1997) Blood 89(1):235-242.

Receptor molecules capable of binding the apo and holo forms of TC II or preferentially or specifically binding the holo-TC II form may similarly be used. Suitable receptors are cell surface or membrane bound TC II or holo-TC II receptors and cross species reactivity properties mean that such receptor molecules from any mammalian species may be used, although preferably the origin of such receptors is human or bovine. Although the receptor molecules are preferably isolated in a relatively purified form, the use of cell membranes or mixed membrane fractions comprising the receptors preferably in concentrated form is also contemplated. Such receptors or receptor containing membranes or membrane fractions may advantageously be isolated from kidney, placenta or tumor cells. Deposit cells should not generally be used as a source of such receptors. Deposit cells may however be used as a source of haptocorrin receptors.

A membrane fraction enriched in TC-II receptor can be obtained as described by Seligman et al., J. Biol Chem 253:1766-1772 (1978) and Nexø et al., Biochem Biophys Act 628: 190-200 (1980). Essentially, tissue, e.g. human placenta or rabbit liver, is cut into small pieces and homogenized in tris buffer, pH 7.4 containing 0.15M NaCl and 10' mM EDTA, followed by centrifugation at 25,000×g for 30 minutes. To remove residual blood the homogenization/centrifugation is repeated at least one time. This membrane fraction is further extracted with detergent, e.g. Ammonyx-LO, Triton X-100 or Chapso, and clarified by centrifucation at 100,000×g for 30 minutes at 4° C. The supernatant is used as the source for TC-II receptor.

An example of a suitable receptor molecule which preferentially binds the holo-TC II complex is the 62 kDa single chain glycoprotein which exists as a noncovalent homodimer and is found on the cell surface of all tissues (Rothenberg & Quadros (1996) Balliere's Clinical Haematology 8 (3) 499-514; WO 96/085150). A further protein suitable for use in the assay method of the invention is gp300, a 600 kDa endocytosis mediating membrane protein which is expressed in absorptive epithelial cells for example, cells of the renal proximal tubule as disclosed and described by Moestrup et al., (1996) Proceedings National Academy Science 93: 8612-8617). This receptor is an LDL receptor and binds both the apo and holo forms of TC II.

Where a cell surface receptor is used, it can be immobilized by conjugation to a surface, e.g. of a bead or sheet, or alternatively a cell membrane fraction containing the receptors may be formed into vesicles or sheets displaying the receptors.

Where the ligand is immobilized, this may for example be on the surface of a solid, e.g. a filter film or sheet or the lumen of a tube, however immobilization on particles, e.g. microspheres such as those produced by Dyno Industrier ASA, Norway, is especially preferred. Such particles may be porous or non-porous and if desired may be provided with means which enable them to be collected, e.g. by inclusion with the particles of magnetically responsive material, for example superparamagnetic iron oxide crystals. Such magnetically responsive microbeads are available from Dyno Industrier ASA as well as from Dynal A S, Norway, Bang Particles, USA and Prolabo, France. Where the ligand is to be immobilizable as opposed to immobilized, this may be achieved by coupling the ligand to a member of a specific binding pair (e.g. biotin/streptavidin) and using the other member of the binding pair, optionally bound to a substrate, to agglomerate or otherwise immobilize the ligand or the ligand:TC II or ligand: holo-TC II complexes, prior to separation of the ligand bound fraction from the non bound fraction in the performance of the method of the invention.

It is well known in the art to immobilise affinity molecules e.g. antibodies and antibody fragments for separation purposes, for example by binding or coupling the ligands, optionally by means of a linker, to any of the well known solid supports or matrices which are currently widely used or proposed for separation or immobilisation on columns and any known method in the art could be used. Such solid phases may take the form of particles, sheets, gels, filters, membranes, fibres or capillaries or microtitre strips, tubes or plates of wells etc and conveniently may be made of glass, silica, latex or a polymeric material. Techniques for binding the ligand to the solid support are also extremely well known and widely described in the literature.

Coupling of the ligand to a substrate or to one member of a specific binding pair may be achieved using conventional techniques.

The method of the invention, if the assay is performed as a competitive binding assay, will generally involve addition to the sample of a labelled compound which competes for binding to the ligand. Generally, it will be preferred to use labelled holo-TC II in this regard. The label used may be any label which can be determined directly or indirectly, e.g. a chromophore (which term is used to include fluorophores), a radiolabel (generally covalently bound or chelate-bound), an enzyme or enzyme substrate, a magnetic label, etc.

A preferred embodiment, the method of the present invention involves contacting an immobilised or an immobilisable TC II or holo-TC II binding ligand with the sample under investigation;

separating a ligand-bound fraction from a non-ligand-bound fraction;

dissociating bound cobalamin from the holo-TC II molecules in the bound fraction and determining the concentration of cobalamin released, preferably with dissociation being so affected that the concentration of the released cobalamin is at least 3 times, preferably 5 times and even more preferably 10 times greater than the concentrations of holo-TC II in the initial sample.

The essence of this aspect of the invention is the separation and concentration of TC II or holo-TC II which allows standard methods of cobalamin determination to be usefully employed in the method. As indicated above, in the absence of such a concentration step state of the art methods are not suitable for cobalamin determination since it exists at such a low concentration. Any appropriate means for releasing cobalamin from the holo-TC II may be used but conveniently heat or changing the pH of the surrounding medium may be used in this regard. The different cobalimin forms may be converted to the less light sensitive cyanocobalamin by treatment with KCN. Any appropriate means for free cobalamin determination may be employed in the method of the invention for example a competition assay performed by contacting an immobilised binding partner for cobalamin with the dissociated cobalamin of the sample in the presence of labelled ligand which competes with the isolated cobalamin for binding to the immobilised binding partners. A method as described by Kuemmerk et al. (1992) Clin. Chem 38:2073-2077 for example would be appropriate. An alternative means for determining free cobalamin is described in U.S. Pat. No. 5,451,508 and involves a immunoassay technique.

In this embodiment of the invention it is preferred that the binding ligands for TC II are immobilised and bind to both holo and apo-TC II.

In an alternative preferred embodiment, the assay method of the present invention comprises contacting a solid support having immobilised thereon a TC II or holo-TC II binding ligand, with the sample under investigation and also with a non-immobilised ligand, wherein said immobilised ligand is capable of binding to TC II or holo-TC II, to said non-immobilised ligand or to complexes of said TC II or holo-TC II and said non-immobilised ligand, and said non-immobilised ligand is capable of binding to at least one of said immobilised ligand, TC II or holo-TC II and complexes of said immobilised ligand and TC II or holo-TC II;

wherein if said assay method is a sandwich assay, at least one of said ligands is specific for holo-TC II and if said assay is a competition assay said immobilised ligand is specific for holo-TC II and competitors thereof;

whereby the proportion of said immobilised ligand bound by TC II or holo-TC II, by said non-immobilised ligand or by complexes of said non-immobilised ligand and TC II or holo-TC II is dependent on the amount of holo-TC II present in said sample, and, said non-immobilised ligand is capable of generating a directly or indirectly detectable signal when bound or when unbound;

separating a bound fraction from a non-bound fraction; and directly or indirectly determining the non-immobilised ligand bound to the immobilised ligand (the bound fraction) or non-bound and in solution (the non-bound fraction);

where the contacting of the sample and said non-immobilised ligand with the solid support may be performed separately, simultaneously or sequentially, and if performed separately or sequentially, they can be contacted in either order.

In essence therefore, the alternative preferred embodiment of the method of the invention involves determining the non-immobilised ligand which has either directly or indirectly bound or alternatively failed to bind directly or indirectly to the immobilised ligand. Where the non-immobilised ligand competes for binding to the immobilised ligand with the holo-TC II, a high level of unbound non-immobilized ligand is indicative of a high concentration of holo-TC II in the sample and a low level of unbound non-immobilized ligand is indicative of a low concentration of holo-TC II in the sample. Where the non-immobilised ligand binds to the TC II or holo-TC II which is bound in turn to the immobilised ligand, then a high level of bound non-immobilized ligand is indicative of a high concentration of holo-TC II in the sample and a low level of bound non-immobilized ligand is indicative of a low concentration of holo-TC II in the sample.

In the method of the present invention therefore, the metabolically active pool of cobalamin is determined by measuring the holo-TC II complex or measuring the amount of cobalamin bound to TC II molecules, present in a body sample which contains a mixture of both apo and holo-TC II and apo and holo-HC (haptocorrin or TC I and III).

A preliminary separation step may be carried out using immobilised cobalamin or an analogue or fragment thereof which selectively binds to the apo-forms of both TC II and haptocorrin (HC). In such a preliminary step, the apo forms of the TC II and HC proteins are bound by the immobilised cobalamin, analogue or fragment thereof and separated from the holo-TC II and holo-HC complexes.

In this case, analysis of the separated holo-forms of TC II then takes place according to any embodiment of the invention as described above but clearly it is most useful where determination of the holo-TC II complex takes place by other than dissociation of the complex and subsequent determination of the released cobalamin. It will be apparent to the skilled person that if such a preliminary step precedes the above-mentioned alternative preferred embodiment, the requirement for at least one ligand in a sandwich assay to be specific for holo-TC II as opposed to TC II and the requirement for the immobilised ligand in a competition assay to be specific for holo-TC II and competitors thereof as opposed to TC II is no longer relevant since the apo-form of TC II has been captured and is no longer available. Thus, the immobilised or non-immobilised ligands may be specific for holo-TC II or TC II or competitors thereof.

The immobilised cobalamin should not exhibit any significant tendency to become dissociated from its support since this could result in binding to apo-TC II and transformation thereof to holo-TC II. Biotinylated cobalamin binds in a very stable manner to a solid surface with avadin/streptavidin bound thereto, and tethering cobalamin to a support in this manner is convenient for the performance of this step. In fact, when biotinylated cobalamin is used, can be added to the sample under analysis in a non-immobilised form where it binds to the apo-forms of TC II and HC. The sample may then be contacted with a solid surface having a binding partner for the biotin example, avidin, immobilised thereon. A complex of avadin-biotinylated cobalamin-TC II then forms which can be easily isolated from the sample.

In one embodiment of the invention wherein this preliminary separation step has taken place, the holo-TC II pool is subsequently determined by contacting the sample with an immobilised TC II ligand which captures the holo-TC II complex leaving the haptocorrin in solution and then contacting the immobilised holo-TC II with a second TC II ligand which is labelled and thus detectable. Examples of suitable TC II binding ligands would be non-overlapping monoclonal antibodies or indeed a polyclonal antibody specific for TC II would be suitable in this embodiment for both capture and detection since different epitopes on the TC II molecules are recognised.

In another embodiment of the invention wherein this preliminary separation step has taken place, the holo-TC II molecules compete with the labelled non-immobilised ligand for binding to the immobilised ligand therefor and the amount of holo-TC II is calculated in relation to the amount of labelled non-immobilised ligand bound or not bound to the immobilised ligand.

In a preferred embodiment, in the preliminary separation step, the binding of apo TC II and apo HC to cobalamin, analogues or fragments thereof takes place at a site or in such a manner which inhibits subsequent recognition and binding of the immobilised cobalamin bound TC II by the non-immobilised ligand or binding partner for TC II. In this embodiment there is no need to isolate the holo-TC II and holo-HC from the bound apo forms before performing the assay of the invention. In this embodiment, the site against which the non-immobilised binding partner or ligand is directed is very important and should be an epitope on TC II which becomes masked or shielded or otherwise unavailable for binding when the apo TC II and apo-HC becomes immobilised on the cobalamin, analogue or fragment thereof.

Whether the initial separation step involves using a binding ligand for TC II or it is preceded by a preliminary step using immobilised cobalamin, analogues or fragments thereof, total separation, ie. separation of all the apo and holo TC II proteins, from the sample, is not a requirement of the method and it suffices that a fraction is separated from the sample which comprises at least a portion of the desired 'TC II subset of proteins'.

Thus, in certain embodiments, the binding partners or ligands and binding conditions may be selected so as to achieve separation of substantially all of the selected "subset". In this case the non-bound fraction may be regarded as being substantially free of TC II or holo-TC II proteins, i.e. being at least 80%, 90% or 95% free of either TC II or holo-TC II depending upon which component is selected as the basis of fractionation.

In alternative embodiments, the binding partner and conditions may be selected so that only a part of the TC II proteins in the sample are separated into a fraction. In this case, account should be taken of the partial separation in constructing a standard calibration curve for the assay. In this regard, the generation of a standard calibration curve against which the concentration of the holo-TC II detected can be determined uses standard techniques well known in the art.

Thus, if in a fractionation step, a TC II binding ligand is used, at least a portion of the TC II bound cobalamin will be located in the bound fraction and any cobalamin in the sample bound to molecules other than TC II, for example, HC or albumin will be in the non-bound (ie. non-separated fraction or fractions). TC II in the bound fraction may be in either apo and holo form and may be complexed by cobalamin like substances or analogues in addition to cobalamin.

If desired, the method of the invention may involve a further preliminary separation step in which the sample is contacted with an immobilized or immobilizable specific binding ligand for haptocorrin (in apo and holo forms or in holo form alone). In this way any contribution to errors in the TC II-bound cobalamin determination deriving from holo-HC may be reduced and specific binding ligands for TC II or holo-TC II may be used which have some binding affinity for haptocorrins.

Otherwise, as indicated above, since the serum concentration of TC II both in apo and holo form is very low, ligands or binding partners of particularly high specificity and affinity are necessary for the operation of the invention. Also, the affinity constants required of the ligands of the present invention depend upon whether the ligand is specific for TC II or holo-TC II and also its utilization as either a capture or detection ligand, since the serum concentration of TC II is about 0.5-1 nM but the concentration of holo-TC II only 35-160 nM. Thus, for a TC II capturing ligand an affinity constant of at least $10^9 M^{-1}$, preferably greater than $2 \times 10^9 M^{-1}$ and more preferably $10^{10} M^{-1}$ is desirable. For a holo-TC II capturing ligand, an affinity constant of at least $10^{10} M^{-1}$ is desirable, preferably $2 \times 10^{10} M^{-1}$, more preferably greater than $2 \times 10^{10} M^{-1}$ and most preferably greater than $10^{11} M^{-1}$. Clearly the affinity constant required of a detecting binder may be less than that of a capturing ligand due to the concentration effect of the assay.

The degree of cross reactivity of a holo-TC II or TC II binding ligand with HC should preferably be less than 1%, more preferably between 0.1% and 1% and most preferably less than 0.1%. Similarly, a holo-TC II binding ligand should preferably not exhibit a degree of cross reactivity with apo-TC II in excess of 1%, more preferably between 0.1% and 1% and most preferably the cross-reactivity should be less than 0.1%.

By using such high affinity ligands their function is extended beyond that of simply being capture and/or detection ligands and they play a vital role in being able to separate and concentrate TC II protein from the sample for analysis. The binding ligands for TC II or holo-TC II should preferably concentrate the ligand by at least 3-fold, more preferably 5-fold, and even more preferably by at least 10-fold.

In a further embodiment of the assay technique more akin to a displacement assay than a competition assay, the sample comprising the holo-TC II complex is contacted with a solid phase to which a labelled ligand recognising the same binding sites on the immobilised ligands as holo-TC II, is bound. The holo-TC II in the sample competes with the bound labelled ligand for the sites such that after equilibration of the system, there is a directly proportional relationship between the amount of labelled ligand displaced from the solid support and detectable in solution and the amount of holo-TC II present in the original sample. The labelled ligand may be detected directly or indirectly and may be determined as the amount of labelled ligand bound or not bound to the solid support as appropriate. In effect, in this embodiment, the non-immobilised ligand referred to earlier is bound to the immobilised ligand before application of the sample but such binding should not be construed to mean that the ligand is in any way immobilised.

A further preferred embodiment involves contacting a holo-TC II containing sample with a solid support having holo-TC II immobilised thereon and a labelled un-immobilised holo-TC II specific binder. The free holo-TC II in the sample and the immobilised holo-TC II complete for binding with the labelled non-immobilised ligand and determination of the labelled ligand bound the solid phase or remaining in solution allows calculation of the holo-TC II concentration. In a particularly preferred embodiment of the present invention the labelled non-immobilised holo-TC II binding ligand is an antibody.

In yet another embodiment, the sample comprising the analyte of interest is contacted with labelled holo-TC II and immobilised ligand. The labelled and non-labelled holo-TC II compete for binding to the immobilised ligand and after equilibrium is reached, the amount of labelled holo-TC II bound to the immobilised ligand is indirectly proportional to the amount of holo-TC II in the sample of interest. Again, the labelled holo-TC II may be detected directly or indirectly and may be determined as the amount of labelled holo-TC II bound or not bound to the solid support as appropriate.

In a further embodiment of the present invention, a non-immobilised but immobilizable ligand specific for the holo-TC II complex, (e.g. a ligand conjugated to biotin or another member of a specific binding pair) is contacted with the sample to form a holo-TC II/non-immobilised ligand complex. The ligand/holo-TC II complex may then be precipitated from solution using known means and isolated for analysis.

In yet another embodiment of the invention, two labelled binding partners are added to the sample, optionally after a preliminary step such as depleting the sample of the apo forms of TC II and HC. The binding partners in this case are labelled holo-TC II or an analogue or fragment thereof and a labelled binding partner therefor, for example a labelled antibody. In this embodiment a detectable signal is only generated from the labels when they are in close proximity to each other ie. when the two labelled binding partners become bound to each other. Thus, on addition to the sample, the labelled binding partner for holo-TC II may bind either to unlabelled holo-TC II present in the sample in which case no detectable signal is generated or to labelled holo-TC II or an analogue, fragment or variant thereof which binds the labelled TC II binding partner, in which case a detectable signal is generated. Labelling agents such as those of Amersham scintillation proximity assays as described in U.S. Pat. No. 4,568,649 are suitable for incorporation into such an embodiment and the high sensitivity of this procedure is well suited to an assay wherein the analyte exists at such a low concentration. Thus for example, one member of the binding pair could be labelled with a β-emitting nuclide such as $I^{125}$ or $H^3$ and the other member is labelled with a suitable scintillant molecule. The emitted β particle loses its energy in its aqueous surroundings unless the scintillant is within 1.5 μm and thus requires both labelled partners to be bound to each other for a signal to be detectable. The probability of two labelled partners binding each other is determined by the concentration of holo-TC II present in the sample such that the greater the signal generated, the lower the concentration of holo-TC II in the sample.

As used herein, the terms "determining" or "assessing" include both quantitation in the sense of obtaining an absolute value for the amount or concentration of holo-TC II or TC II bound cobalamin in the sample, and also semi-quantitative and qualitative assessments or determinations. An index, ratio, percentage or similar indication of the level or amount of TC II bound cobalamin, for example relative to total cobalamin, may be obtained.

The body sample used in the assay method of the invention may be any cobalamin containing sample e.g. a body fluid or tissue sample, or a suspension etc. Preferably, however the sample will be a body fluid for example, seminal fluid, cerebro-spinal fluid or amniotic fluid, but will generally be a blood derived sample. When this is the case, as the sample used for analysis is preferably cell-free, either serum or plasma may be used. The sample may be treated prior to being used in the assay method of the invention, for example it may be diluted by adding a buffer or other aqueous medium and may be stored or preserved for example by chilling or freezing prior to analysis.

In the practise of the invention, where a bound fraction is separated from an unbound fraction this may be performed by any suitable means, for example, precipitation, centrifugation, filtration, chromatographic methods etc.

For the avoidance of doubt, the term "cobalamin" is used herein synonymously with "vitamin $B_{12}$" and includes all forms of vitamin $B_{12}$ (cyanocobalamin; 5-6-dimethyl-benzimidazolyl cyanocobamide; methylcobalamine; 5'-deoxyadenosylcobalamin) as may occur and be metabolically active (when appropriately presented) in the body.

As indicated above, in the method of the invention, the determination of the TC-bound cobalamin may be performed by detecting a ligand bound to the separated holo-TC II, or by performing a competition assay using a labelled competitor to holo-TC II whereby the holo-TC II competes with the labelled competitor for binding to a binding ligand therefor, or by detecting cobalamin released from separated holo-TC II.

The detectable ligand may conveniently be labelled by any conventional means, for example with a signal forming label which may be determined by e.g. luminescence, chemiluminescence, colorimetric assessment, fluorescence, radioactivity or by enzymic activity. In effect, any signal forming label known in the art may be used in the method of the invention.

By means of example only, some suitable examples of coloured or fluorescent compounds which may be used to label a binding ligand detectably in the present invention are anthraquinones, azodyes, azine dyes such as oxazines and thiazines, triazines, naturally occurring pigments such as porphyrins, phycobiliproteins, including phycoerythins and phycoquanins, chlorophylls and their analogues and derivatives, carotenoids, acrinidines, xanthenes including fluoresceins and rhodamines, indigo-dyes, thioxanthenes, coumarins, polymethines including di and tri arylmethines and derivatives thereof of phthalocyanines and metal phtalocyanines.

Similarly, a wide range of radioactive compounds may be used as the signal forming label part of the reagent used in this invention, among them Iodine-125-labelled compounds.

Alternatively, the binding ligands may be conjugated to natural or synthetic compounds which can produce a chemiluminescent signal which may be assayed in known manner (Cormier, M. J. et al.; Chemiluminescence and Bioluminescence, Plenum Press, New York 1973). Suitable chemiluminescent compounds include luciferin, oxalic esters, 1,2-dioxethane, luminol or derivatives thereof, but are not limited to these. If appropriate, hydrogen peroxide, enzymes e.g. luciferase, or other chemicals may be used to produce the chemiluminescent signal from the signal-producing molecules used.

Strongly-anionic signal forming molecules may not be preferred for use in the method of the invention, since they have a tendency to bind to serum proteins such as human serum albumin (HSA) which may be present in the sample. Particularly suitable examples which may be used are fluorescein isothiocyante, Rhodamine B or N-(resorufin-4-carbonyl)piperidine-4-carboxylic acid-N-hydroxysuccinimide-ester) or resos.

In accordance with one embodiment of the method of the invention, a fraction comprising at least a portion of the TC II may be separated from a body fluid sample by reacting the body fluid with a binding ligand specific for TC II and then separating the TC II bound fraction from the rest of the sample, thereby isolating and concentrating the target analyte therein. In one embodiment of the invention, a detectable binding ligand directed against holo-TC II may be used to determine the TC II-cobalamin complex present in the separated bound fraction. The holo-TC II binding ligand may be contacted with the sample under investigation prior to, simultaneously with or after contact with the TC II binding ligand and before or after separation of the TC II bound fraction from the rest of the sample.

Correspondingly, a cobalamin containing fraction (e.g. comprising holo-TC II and holo-HC) may be separated from the rest of the sample by reacting the body fluid under investigation with an immobilised or tethered cobalamin or an analogue or fragment thereof which binds apo-TC II and apo-HC and separating from the bound fraction the rest of the sample which comprises holo-TC II and holo-HC. A detectable TC II binding ligand can then used to detect the TC II-cobalamin complex present in the separated fraction. The detectable TC II binding ligand may be contacted with the sample under study prior to, simultaneously with or after contact with the bound cobalamin and before or after separation of the bound fraction from the rest of the sample.

In some embodiments, immobilised ligands for one or the other components of the apo and/or holo TC II/HC complexes may be arranged in a column. The body fluid containing the TC II cobalamin complex may be applied to the column and contacted with the binding ligand(s).

The column may be flushed through or washed and an eluent used to allow, if necessary, release of a bound fraction from the column and facilitate its collection. If the contents of the unbound fraction are or are also to be analysed with respect to other constituents, the column should be washed with a buffer or medium administered using a calibrated micropipette to ensure a precise known volume is administered and collected. The volume administered is preferably within 3% of the desired (ie. calibration) volume, more preferably within 1 or 2%. Likewise, if the fraction to be analysed is to be released from the column prior to detection, the eluant used to release the complex should be administered using a calibrated micropipette.

In an alternative embodiment, the binding ligands used to separate a fraction of a sample may be immobilised on a particulate solid phase support, for example latex or polymer beads. To aid manipulation and separation, magnetic beads may be used and indeed this is a preferred embodiment of the present invention. the term "magnetic" as used herein means that the support is capable of having a magnetic moment imparted to it when placed in a magnetic field. In other words, a support comprising magnetic particles may readily be removed by magnetic aggregation, which provides a quick, simple and efficient way of separating the fractions following ligand binding.

Thus, using the method of the invention, the magnetic particles with the TC II-cobalamin complex attached may be removed onto a suitable surface by application of a magnetic field, for example, using a permanent magnet. It is usually sufficient to apply a magnet to the side of the vessel containing the sample mixture to cause the particles to congregate at the wall of the vessel and so isolate them for further analysis.

Especially preferred are superparamagnetic particles for example those described by Sintef in EP-A-106873, as magnetic aggregation and clumping of the particles during the reaction can be avoided. The well-known magnetic beads made by Bang Particles (US) may be particularly suited to use in the present invention.

In general, besides the sample under evaluation, calibration samples with known holo-TC II complex content will also be assessed in the performance of the assay method of the invention. Such determinations can be used to plot a calibration curve from which the TC II bound cobalamin content of the sample under investigation may be determined. The nature of the calibration samples and selection of conversion or adjustment factors used in the determination of the holo-TC II complex may vary depending, for example, on the particular ligands used in the binding and separation steps of the assay and other aspects of the method which affect the binding and separation of the sample, for example, buffer composition, assay conditions etc. Typically, calibration samples having holo-TC II contents of 0 to 300 pmol/l will be used. The reference range within which the value for TC II bound cobalamin will generally be found is 30 to 160 pmol/l.

The holo-TC II calibration standard may typically be human, native or recombinant holo-TC II. The use of holo-TC II as a calibrator in holo-TC II assays is novel and forms a further aspect of the invention.

Viewed from a yet further aspect, the invention provides a kit for a diagnostic assay according to the invention, said kit comprising:

an immobilized or immobilizable specific binding ligand for TC II or holo-TC II;

preferably a holo-TC II solution of known concentration and more preferably a set of such solutions having a range of holo-TC II complex concentrations;

optionally, a release agent to release cobalamin from holo-TC II; and optionally a labelled ligand.

The assay method of the invention determines the metabolically active pool of cobalamin by determining the holo-TC II complex or isolating the holo-TC II complex and then determining the cobalamin associated therewith and thus provides a convenient method for the determination of cobalamin deficiency before or after the onset of clinical manifestations of cobalamin deficiency. The assay method may be advantageously used prior to the onset of symptoms since it has an accurate predictive value of negative cobalamin balance.

BRIEF DESCRIPTION OF THE DRAWINGS

The present invention will now be illustrated by the following non-limiting Examples and the accompanying drawings in which.

EXAMPLE 1

Antibodies (e.g. monoclonal or polyclonal antibodies) specific for TC II are immobilized on magnetizable particles.

An aliquot of serum (100-500 µl) mixed with an equal volume of PBS is allowed to react for 15 min with an excess of the immobilized antibody and an excess of a non-overlapping anti-holo-TC II antibody (e.g. a monoclonal antibody) radiolabelled with $I^{125}$. The magnetizable particles are sedimented by using a strong magnet, the supernatant is removed, and the particles are washed with PBS.

The radioactivity is measured and the holo-TC II concentration of the sample is determined by interpolation on a standard curve.

EXAMPLE 2

Antibodies (e.g. monoclonal or polyclonal antibodies) specific for TC II are immobilized on magnetizable particles. An aliquot of serum (600 µl) mixed with an equal volume of PBS is allowed to react with the antibody for 30 min. The magnetizable particles are sedimented by using a strong magnet and the supernatant removed. The particles are washed once with PBS and are subsequently treated with sodium hydroxide (0.3 M) containing potassium cyanide (100 µM), dithiothreitol (15 mM), and a fixed amount of cyanocobalamin radiolabelled with $I^{125}$ or $Co^{57}$ in a total volume of 100 µl for 15 min, to release cobalamin bound to the immobilized holo-TC II and at the same time convert all forms of cobalamin to cyanocobalamin and mix with a fixed amount of labelled cyanocobalamin. A limited amount of Intrinsic Factor in 100 µl of borate buffer is added and allowed to react for 10 min. The magnetizable particles are sedimented by a strong magnet and 150 µL of the supernatant removed for measuring radioactivity. The concentration of TC II-bound cobalamin in the serum sample is determined from a standard curve.

Alternatively the released cobalamin may be measured using Abbot's IMx method or similar methods.

EXAMPLE 3

Antibodies (e.g. monoclonal or polyclonal antibodies) specific for holo-TC II are immobilized on magnetizable particles. To an aliquot of serum (100-500 µL) mixed with an equal volume of PBS is added a fixed amount of $I^{125}$ labelled holo-TC II and a limited amount of the immobilized anti-holo-TC II antibody. After incubation for 15 min the magnetizable particles are sedimented by using a strong magnet. The particles are washed with PBS, and the radioactivity measured. The concentration of holo-TC II is determined from a standard curve.

EXAMPLE 4

Recombinant holo-TC II is immobilized on magnetizable particles. To an aliquot of serum (100-500 µL) mixed with an equal volume of PBS is added a fixed amount of immobilized holo-TC II and an excess of an antibody (e.g. a monoclonal or polyclonal antibody) specific for holo-TC II and radiolabelled with $I^{125}$. After 15 min incubation the particles are sedimented by using a strong magnet. The particles are washed with PBS, and the radioactivity measured. The concentration of holo-TC II is determined from a standard curve.

EXAMPLE 5

To an aliquot of serum (100-500 µL) is added an excess of biotinylated cobalamin, so as to bind all apo-TC II and apo-HC. After incubation for 10 min, the serum sample is treated with avidin coated magnetic particles for 10 min. The particles are sedimented by using a strong magnet. The supernatant is recovered and mixed with two non-overlapping monoclonal anti-TC II antibodies, one radiolabelled with $I^{125}$ and the other with conjugated biotin. After 10 min avidin-coated magnetizable particles are added and allowed to bind the biotinylated adducts for 10 min. Subsequently, the particles are sedimented with a strong magnet and washed with PBS. The radioactivity is measured and the holo-TC II concentration is determined by interpolation on a standard curve.

EXAMPLE 6

Same as Example 5, but the apo-TC II depleted serum is mixed with a fixed amount $I^{125}$ labelled holo-TC II and a limited amount of anti-TC II antibody immobilized on magnetizable particles. After incubation for 15 min the particles are sedimented by using a strong magnet.

The particles are washed with PBS and the radioactivity is measured.

EXAMPLE 7

Cobalamin is immobilised onto magnetizable microspheres, e.g. by covalent coupling or by using biotin-(Strept)avidin coupling. Typically, Streptavidin coated magnetizable microspheres are incubated with 1 µM biotinylated cobalamin for 30 minutes at room temperature and in the dark. The beads are sedimented by using a magnet, washed twice with PBS and resuspended at 1% in PBS+5 mg/mL HSA. To an aliquot of serum (100-500 µL) is added the same volume of PBS and ⅒th volume of cobalamin coated magnetizable microspheres. The mixture is incubated for 30 minutes at room temperature in the dark so as to bind all apoTCII and apoHC. The particles are sedimented by magnet and the supernate recovered and mixed with two non-overlapping monoclonal anti-human TC II antibodies, one radiolabelled with $I^{125}$ and the other conjugated with biotin. After 10 minutes (Strept) avidin-coated magnetizable microspheres are added and allowed to bind the biotinylated adducts for 10 minutes. Subsequently, the particles are sedimented with a magnet and washed with PBS. The radioactivity is measured and the holo-TC II concentration is determined by interpolation on a standard curve.

EXAMPLE 8

Same as Example 7 but excess biotinylated cobalamin is added directly to the serum sample+PBS, so as to bind all apoTCII and apoHC. After incubation for 10 minutes, the serum sample is treated with (Strept)avidin coated magnetizable microspheres for 30 minutes at room temperature, in the dark.

EXAMPLE 9

Rabbit antibody specific for human TCII and with an apparent binding constant $>5\times10^9$ $M^{-1}$ was immobilized on 1 µm magnetizable microspheres coated with goat anti-rabbitIgG antibody (Indica Diagnostics). Serum samples of 400 µL each from 49 healthy volunteers were mixed with an equal volume of PBS and 40 µL of the immobilized antibody (1%). The mixtures were kept at room temperature in the dark for 1 hour and then microspheres were sedimented by using a magnet. The precipitates were washed once with ice-cold wash buffer (PBS plus 0.02% Tween 20) and subsequently resuspended in 50 µL 50 mM dithiothreitol, 0.001% potassium cyanide, and a fixed amount of 57Co-CN-Cobalamin (Amersham) in phosphate buffer, pH 7.5. This was allowed to stand for 30 minutes at room temperature after which 25 µL 0.5M sodium hydroxide was added and 15 minutes later 300 µL Intrinsic Factor immobilized on Dextran (enough to bind 50% of tracer) in borate buffer, pH 8.6. After 1 hour at room temperature, in the dark, samples were centrifuged at 1000 g and 4° C. for 10 minutes, supernates carefully removed, and pellets counted in a Packard Riastar. The concentration of TCII-bound cobalamin was determined from a standard curve constructed with eight calibrators (0-500 pM of holo TC-II) treated identically to samples. 37 serum samples were also analysed with respect to total serum cobalamin by using the Abbot IMx B12 assay.

Figure 1:
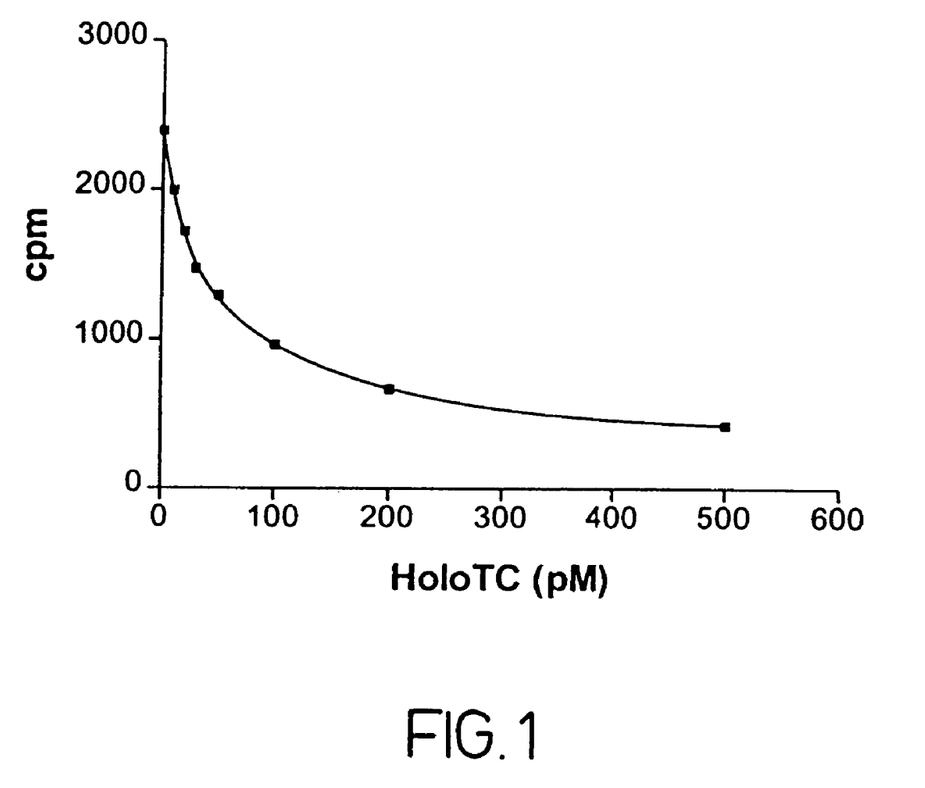
FIG. 1 is a standard curve for holo-TC II.
Figure 2:
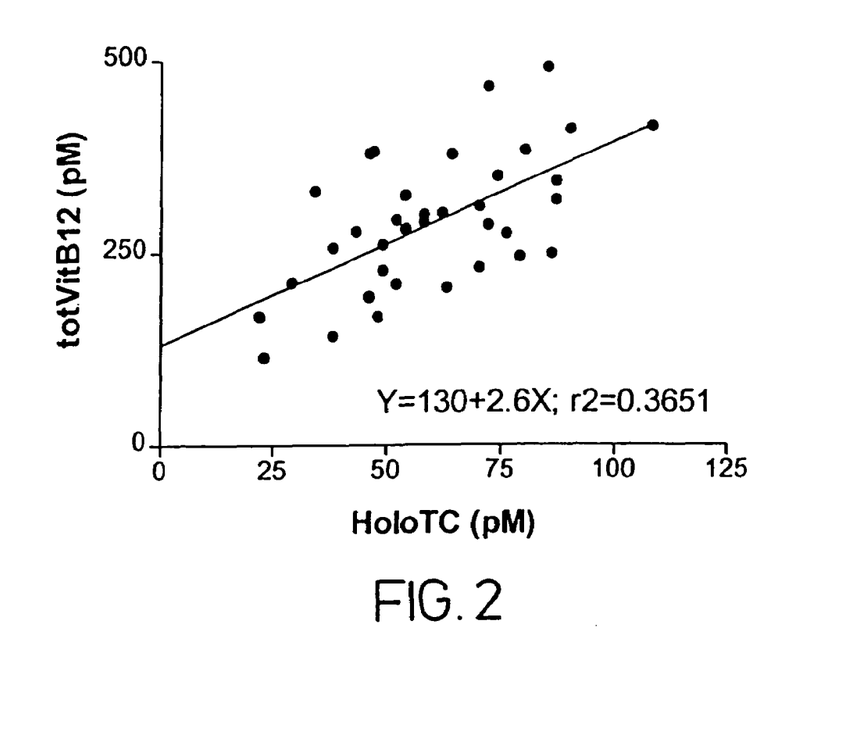
FIG. 2 is a plot showing the relationship between total serum cobalamin and holo-TC II concentration.
Figure 3:
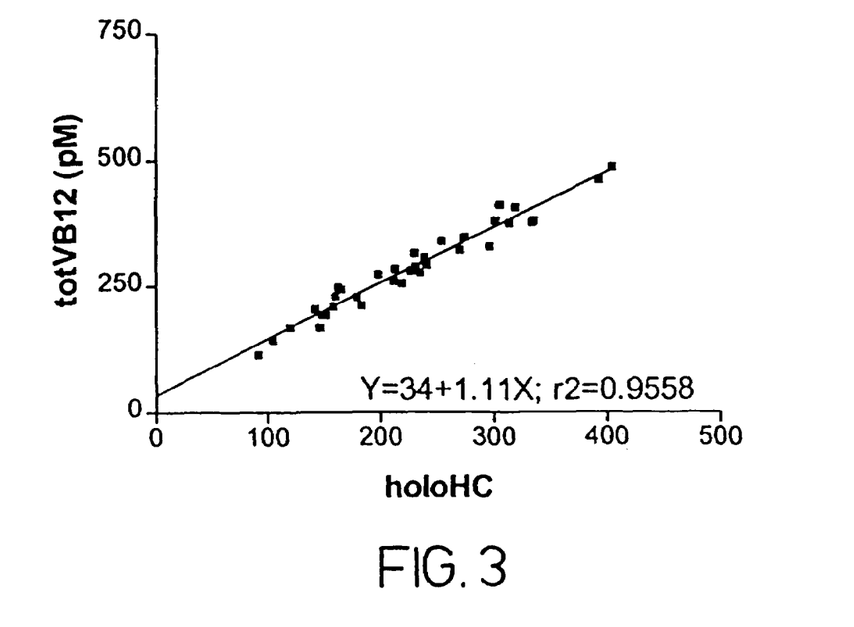
FIG. 3 is a plot showing the relationship between total serum cobalamin and holo-HC concentration.

The standard curve for holo TC-II is shown in FIG. 1 and the relation between total serum cobalamin and holo TC-II concentrations in 37 healthy volunteers is illustrated in FIG. 2. It is evident that the correlation is low, with $r^2=0.50$. In contrast, the correlation between holoHC and total serum cobalamin is high, $r^2=0.96$ (FIG. 3). The average holoTC concentration for the 49 healthy volunteers was 64±28 pM and the 95% reference range 23-127 pM.

The assay has a CV of 10%, an analytical sensitivity (0-calibrator-3 s.d.) below 10 pM and does not cross-react with haptocorrin.

What is claimed is:

1. An assay method for the determination of holo-Transcobalamin II (holo-TCII) in a body fluid sample, comprising:
    contacting a sample of a body fluid with an immobilized cobalamin or an immobilizable cobalamin which is bound to one member of a specific binding pair which selectively binds the apo-forms of TCII and haptocorrin (HC) in said sample over the holo-forms thereof,
    separating said selectively bound TCII from said sample or rendering said selectively bound TCII unable to bind to a specific binding ligand for TCII or holo-TCII,
    contacting the non-bound TCII with a specific binding ligand for TCII or holo-TCII to bind said holo-TCII to form a ligand bound fraction and a non-ligand bound fraction, and
    measuring the TCII content of said ligand bound fraction to determine the quantity of holo-TCII in the body sample being assayed.

2. An assay method as claimed in claim 1 wherein said specific binding ligand is a ligand selected from the group consisting of a polyclonal antibody, a monoclonal antibody, and an antibody fragment.

3. An assay method as claimed in claim 1 wherein said specific binding ligand binds holo-TCII with an affinity constant of at least $10^9 M^{-1}$.

4. An assay method as claimed in claim 1 wherein said specific binding ligand binds holo-TCII with an affinity constant of greater than $10^{11} M^{-1}$.

5. An assay method as claimed in claim 1 wherein the degree of cross-reactivity of said specific binding ligand with HC is less than 0.1%.

6. An assay method as claimed in claim 1 wherein said sample which is contacted with the immobilized cobalamin is further contacted with a solid phase support having immobilized thereon said specific binding ligand and to which is bound a labelled ligand recognizing the same binding sites on the immobilized specific binding ligand as holo-TCII, whereby holo-TCII in said sample competes with said bound labelled ligand for said binding sites such that after equilibration of the system there is a directly proportional relationship between the amount of labelled ligand displaced from said solid phase support and detectable in solution and the amount of holo-TCII present in the original sample; said labelled ligand being detected directly or indirectly as the amount of labelled ligand bound or not bound to said solid phase support as appropriate.

7. An assay method as claimed in claim 1 wherein said sample which is contacted with the immobilised cobalamin is further contacted with a solid phase support having holo-TCII immobilised thereon and with a labeled non-immobilised holo-TCII specific binding ligand, whereby free holo-TCII in the sample and immobilised holo-TCII compete for binding to the labelled non-immobilised ligand; and determination of the labelled ligand bound to the solid phase support or remaining in solution allows determination of the holo-TCII concentration.

8. An assay method as claimed in claim 1 wherein said sample which is contacted with the immobilised cobalamin is further contacted with labeled holo-TCII and an immobilised ligand therefor whereby labelled and non-labeled holo-TCII compete for binding to the immobilised ligand and after equilibrium is reached, the amount of labeled holo-TCII bound to the immobilised ligand is indirectly proportional to the amount of holo-TCII in the sample.

9. An assay method as claimed in claim 1 wherein said body fluid sample is a sample selected from the group consisting of seminal fluid, cerebro-spinal fluid, amniotic fluid and a blood derived sample.

10. An assay as claimed in claim 9 wherein said blood derived sample is serum or plasma.

11. An assay method as claimed in claim 1 wherein said bound fraction is separated from said unbound fraction by precipitation, centrifugation, filtration or chromatographic methods.

12. An assay method as claimed in claim 1 wherein said ligand is labelled with a signal forming label which may be determined by luminescence, chemiluminescence, calorimetric assessment, fluorescence, radioactivity or by enzymic activity.

13. An assay method as claimed in claim 1 in which assay calibration is effected using a holo-TCII standard.

14. An assay as claimed in claim 13 wherein said standard is human, native or recombinant holo-TCII.

* * * * *